United States Patent [19]

Nita

[11] Patent Number: 5,380,274
[45] Date of Patent: Jan. 10, 1995

[54] ULTRASOUND TRANSMISSION MEMBER HAVING IMPROVED LONGITUDINAL TRANSMISSION PROPERTIES

[75] Inventor: Henry Nita, Mission Viejo, Calif.

[73] Assignee: Baxter International Inc., Deerfield, Ill.

[21] Appl. No.: 135,275

[22] Filed: Oct. 12, 1993

Related U.S. Application Data

[63] Continuation-in-part of Ser. No. 640,190, Jan. 11, 1991, Pat. No. 5,304,115.

[51] Int. Cl.$^6$ .............................................. A61B 17/32
[52] U.S. Cl. .................................... 604/22; 601/2; 606/169
[58] Field of Search ......................... 604/21, 22, 52; 606/167–171, 159; 601/2

[56] References Cited

U.S. PATENT DOCUMENTS 3,352,303 11/1967 Delaney .
3,433,226 3/1969 Boyd .
(List continued a next page.)

FOREIGN PATENT DOCUMENTS

| 1531659 | 7/1977 | European Pat. Off. . |
|---|---|---|
| 0424231 | 4/1984 | European Pat. Off. . |
| 189329 | 7/1986 | European Pat. Off. . |
| 293472 | 11/1986 | European Pat. Off. . |
| 208175 | 1/1987 | European Pat. Off. . |
| 0209468 | 1/1987 | European Pat. Off. . |
| 234951 | 2/1987 | European Pat. Off. . |
| 316796 | 11/1988 | European Pat. Off. . |
| 347098 | 6/1989 | European Pat. Off. . |
| 315290 | 10/1989 | European Pat. Off. . |
| 443256 | 12/1990 | European Pat. Off. . |
| 472368 | 2/1992 | European Pat. Off. . |
| 2424733 | 11/1980 | France . |
| 2641693 | 7/1990 | France . |
| 2643272 | 8/1990 | France . |
| 2349120 | 4/1975 | Germany . |
| 2438648 | 2/1976 | Germany . |
| 2453058 | 5/1976 | Germany . |
| 2453126 | 5/1976 | Germany . |
| 2541919 | 3/1977 | Germany . |
| 2703486 | 12/1977 | Germany . |
| 8119209 | 9/1981 | Germany . |
| 3726210 | 8/1987 | Germany . |
| 3707567 | 9/1987 | Germany . |
| 3707921 | 9/1987 | Germany . |
| 3826414 | 2/1989 | Germany . |
| 3812836 | 4/1990 | Germany . |
| 4114826 | 5/1991 | Germany . |
| 1520448 | 6/1987 | United Kingdom . |
| 2208138A | 3/1989 | United Kingdom . |
| 2212267 | 7/1989 | United Kingdom . |
| WO87/01276 | 3/1987 | WIPO . |
| WO87/05793 | 10/1987 | WIPO . |
| WO89/05123 | 6/1989 | WIPO . |
| WO89/06515 | 7/1989 | WIPO . |
| WO89/07419 | 8/1989 | WIPO . |
| WO90/01300 | 2/1990 | WIPO . |
| WO90/07303 | 7/1990 | WIPO . |
| WO91/02489 | 3/1991 | WIPO . |
| WO91/14401 | 10/1991 | WIPO . |
| WO92/10140 | 6/1992 | WIPO . |
| WO92/11815 | 7/1992 | WIPO . |

OTHER PUBLICATIONS

Circulation, vol. 81, No. 2, Feb. 1990, "Application of a New Phased-Array Ultrasound Imaging Catheter in the Assessment of Vascular Dimensions," pp. 660–666.
"Ultrasonic Energy Causes Doe-Dependent, Endothelium-Independent Arterial Relaxation"—T. Fischell, et al. Abstracts of the 63rd Scientific Sessions, pp. 111–219.

Primary Examiner—C. Fred Rosenbaum
Assistant Examiner—Michael Rafa
Attorney, Agent, or Firm—Stetina, Brunda & Buyan; Raymond Sun

[57] ABSTRACT

An elongate ultrasound transmission member having regions of differing cross-sectional dimension or diameter. A sleeve, sheath or other damping member may be positioned around a portion of the ultrasound transmission member to dampen or limit transverse side-to-side movement of such portion of the member. The ultrasound transmission member may be incorporated into a flexible catheter body to form an ultrasound delivering medical catheter.

29 Claims, 3 Drawing Sheets

U.S. PATENT DOCUMENTS

| | | |
|---|---|---|
| 3,526,219 | 9/1970 | Balamuth . |
| 3,565,062 | 3/1971 | Kuris . |
| 3,589,363 | 6/1971 | Banko . |
| 3,618,594 | 11/1970 | Banko . |
| 3,809,093 | 5/1974 | Abraham . |
| 3,823,717 | 7/1974 | Pohlman . |
| 3,861,391 | 1/1975 | Antonevich et al. . |
| 3,896,811 | 7/1975 | Storz . |
| 4,188,952 | 2/1980 | Loschivlov et al. . |
| 4,214,586 | 7/1980 | Mericle . |
| 4,223,676 | 9/1980 | Wuchinich et al. . |
| 4,366,819 | 1/1983 | Kaster . |
| 4,431,006 | 2/1984 | Trimmer et al. . |
| 4,474,180 | 10/1984 | Angulo . |
| 4,587,958 | 5/1986 | Noguchi et al. . |
| 4,587,972 | 5/1986 | Morantte . |
| 4,589,419 | 5/1986 | Laughlin et al. . |
| 4,665,906 | 5/1987 | Jervis . |
| 4,692,139 | 9/1987 | Stiles . |
| 4,750,902 | 6/1988 | Wuchinich et al. . |
| 4,794,931 | 1/1989 | Yock . |
| 4,799,496 | 1/1989 | Hargraves . |
| 4,800,876 | 1/1989 | Fox et al. . |
| 4,808,153 | 2/1989 | Parisi . |
| 4,821,731 | 4/1989 | Martinelli . |
| 4,841,977 | 6/1989 | Griffith . |
| 4,844,092 | 7/1989 | Rydell . |
| 4,870,953 | 10/1989 | DonMichael . |
| 4,898,575 | 2/1990 | Fischell et al. . |
| 4,917,097 | 4/1990 | Proudian et al. . |
| 4,919,133 | 4/1990 | Chiang . |
| 4,920,954 | 5/1990 | Alliger et al. . |
| 4,923,441 | 5/1990 | Shuler . |
| 4,924,863 | 5/1990 | Sterzer . |
| 4,936,281 | 6/1990 | Stasz . |
| 4,957,111 | 9/1990 | Millar . |
| 4,960,411 | 10/1990 | Buchbinder . |
| 4,966,583 | 10/1990 | Debbas . |
| 4,967,653 | 11/1990 | Hinz . |
| 4,967,753 | 11/1990 | Haase et al. . |
| 4,979,939 | 12/1990 | Shiber . |
| 4,988,356 | 1/1991 | Crittenden . |
| 4,998,527 | 3/1991 | Meyer . |
| 5,022,399 | 6/1991 | Biegeleisen . |
| 5,029,588 | 7/1991 | Yock et al. . |
| 5,058,570 | 10/1991 | Idemoto et al. . |
| 5,061,238 | 10/1991 | Shuler . |
| 5,069,664 | 12/1991 | Guess et al. . |
| 5,076,276 | 12/1991 | Sakurai et al. . |
| 5,100,423 | 3/1992 | Fearnot . |
| 5,269,297 | 12/1993 | Weng et al. ............................ 604/22 |

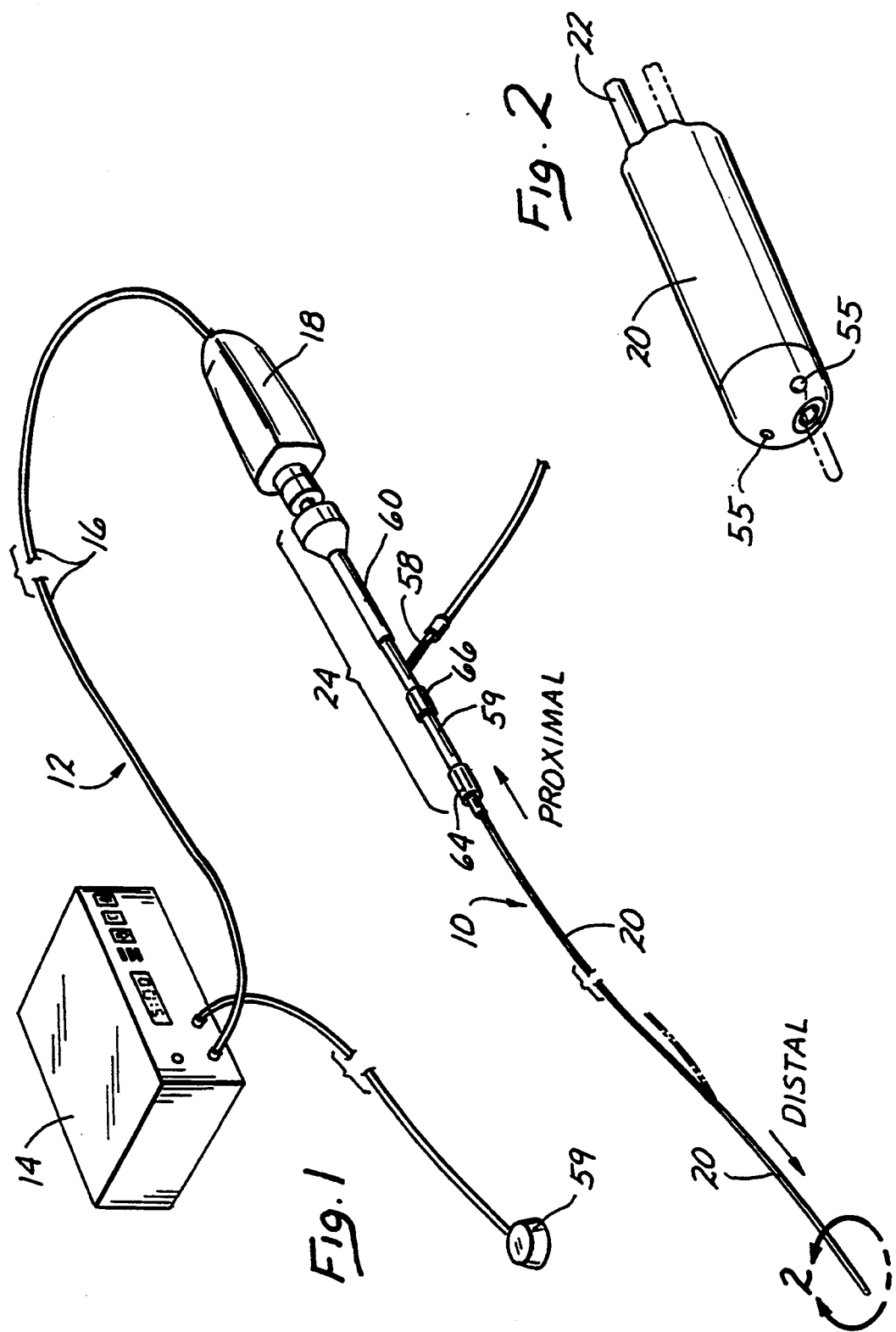

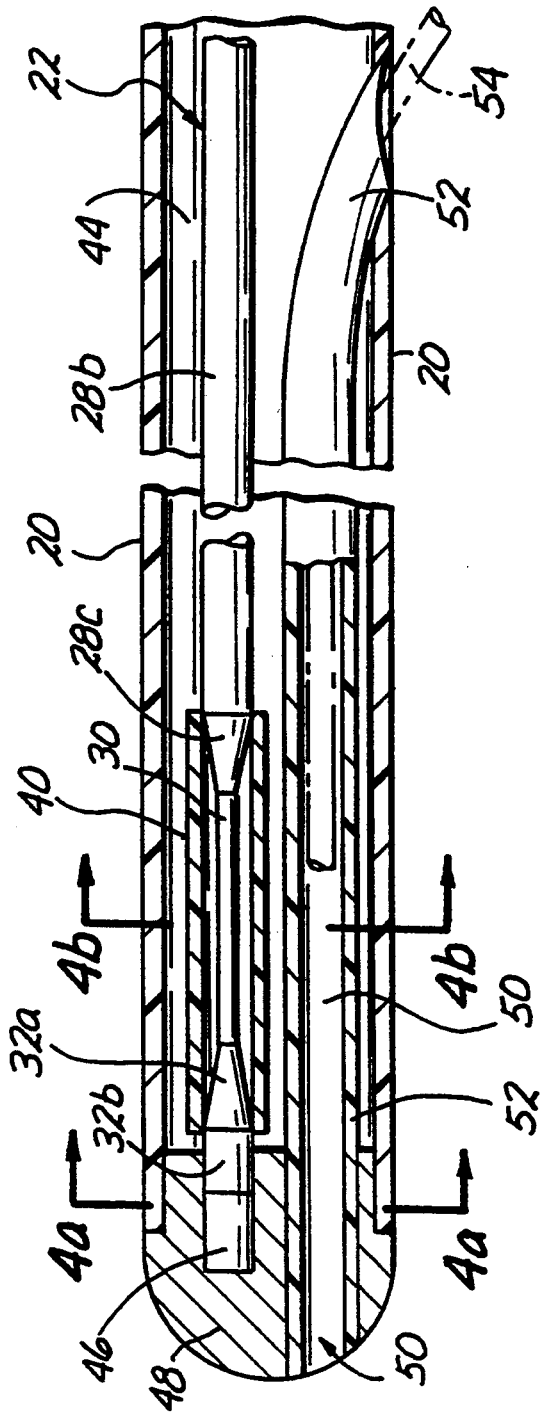

ULTRASOUND TRANSMISSION MEMBER HAVING IMPROVED LONGITUDINAL TRANSMISSION PROPERTIES

RELATED APPLICATION

This patent application is a continuation-in-part of U.S. patent application Ser. No. 07/640,190 entitled ULTRASONIC ANGIOPLASTY DEVICE INCORPORATING IMPROVED TRANSMISSION MEMBER AND ABLATION PROBE, filed on Jan. 11, 1991, U.S. Pat. No. 5,304,115, entire disclosure of which is expressly incorporated herein by reference.

FIELD OF THE INVENTION

The present invention relates generally to medical devices and more particularly to an improved ultrasound transmission member for transmitting ultrasonic energy from an extracorporeal ultrasound generating device to a location within a mammalian body.

BACKGROUND OF THE INVENTION

The prior art has included a number of ultrasonic devices for abating, destroying or removing obstructive material within anatomical structures of the body, such as blood vessels. Examples of devices which purportedly utilize ultrasonic energy, alone or in conjunction with other treatment modalities, to remove obstructions from anatomical structures include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al.), 4,920,954 (Aliiget, et al.), and 5,100,423 (Fearnot) as well as other patent publications W087-05739 (Cooper), W089-06515 (Bernstein, et al.), W090-0130 (Sonic Needle Corp.), EP316789 (Don Michael, et al.), DE3,821,836 (Schubert) and DE2,438,648 (Pohlman).

In particular, flexible ultrasound-delivering catheters have been utilized to recanalize blood vessels which have become obstructed by atherosclerotic plaque and/or thrombotic matter.

Previously filed U.S. patent application Ser. No. 07/640,190, entitled ULTRASONIC ANGIOPLASTY DEVICE INCORPORATING IMPROVED TRANSMISSION MEMBER AND ABLATION PROBE, of which this application is a continuation-in-part, describes percutaneously insertable ultrasound delivering catheters which are useable to ultrasonically ablate or remove obstructive matter from blood vessels. As disclosed in patent application Ser. No. 07/640,190, such ultrasound delivery catheters may be constructed of a flexible catheter sheath having an elongate ultrasound transmission member or wire extending longitudinally therethrough. The cross-sectional dimension of the ultrasound transmission member may be tapered or narrowed near the distal end of the member. While such tapering or narrowing of the cross-sectional diameter of the ultrasound transmission member will typically decrease its rigidity and improve its bendability at the region of the taper or narrowing, such tapering or narrowing of the ultrasound transmission member carries with it a resultant increase in amplitude of the ultrasonic energy being transmitted through such narrowed or tapered region. Such increase in amplitude at the narrowed or tapered region may give rise to an increased likelihood of breakage or fracture of the ultrasound transmission member.

To facilitate use of ultrasonic ablation techniques within small tortuous blood vessels or other anatomical structures, it is desirable to develop small-diameter ultrasound-delivery catheters which are sufficiently pliable and bendable, at least in their distal regions, to navigate tortuous anatomical configurations without undue likelihood of breakage or fracture of the ultrasound transmission member during use.

In view of the foregoing, there remains a need in the art for development of new ultrasound transmission members having improved pliability or bendability with minimal likelihood of breakage or fracture.

SUMMARY OF THE INVENTION

In accordance with the present invention, there is provided an ultrasound transmission member having at least four regions of differing cross-sectional dimension. The main proximal region of the member is of substantially continuous first cross-sectional dimension or diameter. The second region of the member extends distally from the distal end of the first region thereof, and is downwardly tapered to a (continuously or in a stepwise fashion) from said first cross-sectional dimension to a second cross-sectional dimension smaller than said first cross-sectional dimension. A third region of the member extends distally from the distal end of the second region and is of a substantially continuous cross-sectional dimension preferably equal to said second cross-sectional dimension. The fourth region of the member extends distally from the distal end of the third region and is outwardly tapered (continuously or in a step-wise fashion) to a fourth cross-sectional dimension, said fourth cross-sectional dimension being larger than the continuous cross-sectional dimension of said third region.

Further in accordance with the invention, a sleeve, sheath or other damping member may be positioned around the third region of the ultrasound transmission member to dampen or limit transverse side-to-side vibration of the third region during operation.

Still further in accordance with the invention, the ultrasound transmission member may be formed of various materials including super elastic metal alloy. A presently preferred superelastic metal alloy is a nickel titanium alloy containing 50.8 atomic per cent nickel/balance titanium.

Still further in accordance with the invention, the ultrasound transmission member of the foregoing character may be incorporated into a flexible ultrasound catheter, said ultrasound catheter being insertable into a blood vessel or other anatomical structure for purposes of delivering ultrasonic energy to an anatomical structure within the mammalian body.

Still further in accordance with the invention, the ultrasound transmission member of the foregoing character may be incorporated into a guide wire, or other elongate housing or body for purposes of carrying ultrasonic vibration therethrough.

Further objects and advantages of the invention will become apparent to those skilled in the art upon reading and understanding of the following detailed description and the accompanying drawings.

BRIEF DESCRIPTION OF THE DRAWINGS

FIG. 1 is a perspective view of an ultrasound catheter device of the present invention operatively connected to an ultrasound generating system.

FIG. 2 is an enlarged perspective view of the distal end of the ultrasound catheter of FIG. 1 having a guide wire (phantom lines) extending therethrough.

FIG. 3 is a longitudinal sectional view of the distal portion of the catheter shown in FIG. 1.

FIG. 4a is a cross-sectional view through Line 4a—4a of FIG. 3.

FIG. 4b is a cross-sectional view through Line 4b—4b of FIG. 3.

FIG. 6 is a side elevational view of a portion of the ultrasound transmission member of FIG. 5 having a damping member or sleeve positioned thereon.

DETAILED DESCRIPTION OF THE PREFERRED EMBODIMENT

Figure 5:
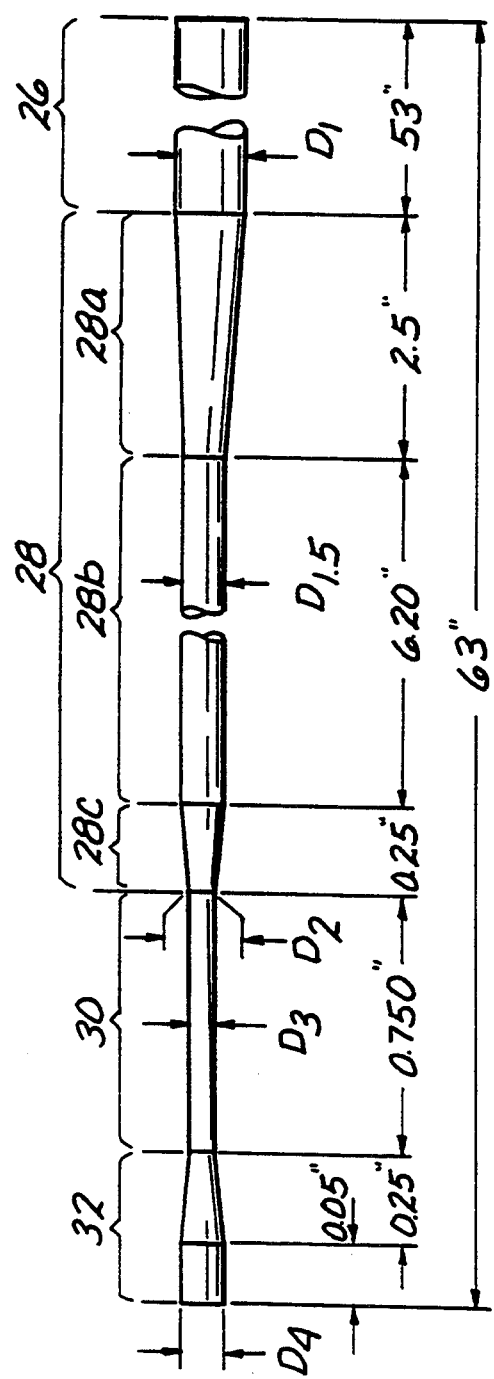
FIG. 5 is a broken elevational view of the distal portion of the preferred ultrasound transmission member of the present invention.

The following detailed description and the accompanying drawings are intended to describe and illustrate presently preferred embodiments of the invention only and are not intended to limit the scope of the invention in any way. Specifically, the hereafter described embodiments and drawings are not intended to comprehensively describe or show all of the possible embodiments of the claimed invention.

A. A Preferred Ultrasound Catheter Incorporating An Ultrasound Transmission Member Of The Present Invention As shown in FIG. 1, an ultrasonic catheter 10 of the present invention may be utilized by coupling the ultrasonic catheter 10 to an ultrasound generating system 12. The ultrasound generating system 12 comprises a signal generator 14 (e.g., Model UAG.1110, Baxter Healthcare Corp., Edwards LIS Division, Irvine, Calif. connected, by way of cable 16 to an ultrasound transducer 18 (e.g., Model UAT-1000, Baxter Healthcare Corporation, Edwards LIS Division, Irvine, Calif.), which is operable to convert the electrical signal into ultrasonic vibration.

The ultrasound catheter 10 of the present invention comprises an elongate flexible catheter body 20 having an elongate ultrasound transmission member or wire 22 extending longitudinally therethrough. A proximal end connector assembly 24 is positioned on the proximal end of the catheter body 10. As shown in detail in FIG. 7 the proximal connector assembly 24 is configured to facilitate connection of the proximal end of the ultrasound transmission member 22 to the ultrasound transducer 18 such that ultrasonic vibration from the transducer 18 will be transmitted, distally, through the ultrasound transmission member 22 to the distal end of the catheter 10.

The ultrasound transmission member 22 of the present invention may be formed of any suitable material capable of carrying ultrasonic energy from the proximal end of the catheter 10 to the distal end thereof. In particular, the presently preferred embodiment of the ultrasound transmission member 22 of the present invention is formed of nickel-titanium alloy which exhibits superelastic properties within the temperature range under which the device is operated.

In particular, one presently preferred superelastic metal alloy of which the ultrasound transmission member 22 may be formed is nickel-titanium alloy consisting of 50.8 atomic percent nickel/balance titanium and is commercially available as Tinel ™ BB from Raychem Corporation, Menlo Park, Calif. The physical properties of the preferred 50.8 atomic per cent nickel NiTi alloy are as follows:

| Properties of NiTi Alloy Having 50.8 At. % Nickel/Balance Titanium | | |
|---|---|---|
| Property* | Units | Value |
| Superelastic Temperature Range | °C. | 20 to 80 |
| Loading Plateau Stress (at 20° C.) | Mpa | 480 |
| Unloading Plateau Stress | Mpa | 135 | connector assembly 24 is positioned on the proximal end of the catheter body 10. As shown in detail in FIG. 7 the proximal connector assembly 24 is configured to facilitate connection of the proximal end of the ultrasound transmission member 22 to the ultrasound transducer 18 such that ultrasonic vibration from the transducer 18 will be transmitted, distally, through the ultrasound transmission member 22 to the distal end of the catheter 10.

The ultrasound transmission member 22 of the present invention may be formed of any suitable material capable of carrying ultrasonic energy from the proximal end of the catheter 10 to the distal end thereof. In particular, the presently preferred embodiment of the ultrasound transmission member 22 of the present invention is formed of nickel-titanium alloy which exhibits super elastic properties within the temperature range under which the device is operated.

In particular, one presently preferred superelastic metal alloy of which the ultrasound transmission member 22 may be formed is nickel-titanium alloy consisting of 50.8 atomic percent nickel/balance titanium and is commercially available as Tinel ™ BB from Raychem Corporation, Menlo Park, Calif. The physical properties of the preferred 50.8 atomic per cent nickel NiTi alloy are as follows:

| Properties of NiTi Alloy Having 50.8 At. % Nickel/Balance Titanium | | |
|---|---|---|
| Property* | Units | Value |
| Superelastic Temperature Range | °C. | 20 to 80 |
| Loading Plateau Stress (at 20° C.) | Mpa | 480 |
| Unloading Plateau Stress | Mpa | 135 |
| Permanent Set (at 20° C. after 8% strain) | % | 0.2 |
| Ultimate Tensile Strength (at 20° C.) | Mpa | 1150 |
| | Ksi | 170 |
| Elongation at Failure | % | 10 |
| Melting Point | °C. | 1350 |
| Density | g/cm | 6.5 |
| | lbs/cu.Inch | 0.235 |

*Typical Values for Cold Worked and Shape Set Condition

Examples of superelastic metal alloys which are useable to form the ultrasound transmission member 22 of the present invention is described in detail in the U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767;

and 4,337,090 are expressly incorporated herein by reference insofar as they describe the compositions, properties, chemistries, and behavior of specific metal alloys which are superelastic within the temperature range at which the ultrasound transmission member 22 of the present invention operate, any and all of which superelastic metal alloys may be useable to form the superelastic ultrasound transmission member 22.

In the preferred embodiment, the ultrasound transmission member 22 is specifically configured and constructed to provide desirable flexibility or bendability near the distal end of the catheter, while at the same time minimizing the likelihood of breakage or fracture of the ultrasound transmission member 24 during use.

For example, one preferred configuration is shown in FIG. 5 for an ultrasound transmission member 22 of the present invention having an overall length of 63. As shown, the ultrasound transmission member 22 having an overall length of 63 inches comprises a) a first (proximal) region 26, b) a second region 28 extending distally from the first proximal region 26, c) a third region 30 extending distally from the second region 28, and d) a fourth region 32 extending distally from the third region 30.

The first (proximal) region 26 of the ultrasound transmission member 22 constitutes the main proximal portion of the member 22, and extends approximately 50.5 inches from the proximal end thereof. The outer diameter D1 of the first portion 26 is approximately 0.030 inches and is substantially continuous over its entire length.

The second region 28 is about 6.2 inches in overall length and is downwardly tapered, from an outer diameter equal to D1 at its proximal end, to a smaller outer diameter D2 at its distal end. The tapering or narrowing of the second region 28 may be gradually continuous or may be formed in steps, as shown in FIG. 5. Specifically, as shown in FIG. 5, the second region 28 includes first 28A, second 28B and third 28C subregions. The first subregion 28A is gradually tapered from diameter D1 to an intermediate diameter D1.5 between D1 and D2. The second subregion 28B is of substantially continuous intermediate diameter D1.5 over its entire length. The third subregion 28C is then further downwardly tapered to a diameter of D2, as shown.

The third region 30 of the ultrasound transmission member 22 is of continuous diameter D3 over its entire length of approximately 0.750 inches. Diameter D3 is the same as diameter D2 at the distal end of the second region 28.

The fourth region 32 of the ultrasound transmission wire 22 is outwardly tapered or enlarged from diameter D3 at its proximal end to diameter D4 at its distal end. The fourth region 32 of the ultrasound transmission member 22 may be of a gradually continuous taper or may include multiple subregions, as shown in FIG. 5. Specifically, as shown in FIG. 5, the fourth region 32 has an overall length of 0.300 inches and comprises a first subregion 32A and a second subregion 32B. In the embodiment shown, the first subregion 32A is gradually tapered from diameter D3 to diameter D4. The second subregion 32B is of substantially continuous outer diameter D4. Diameter D4 is approximately 0.014 inches.

Because the third region 30 of the ultrasound transmission member 22 is of minimal diameter D3, such third region 30 is subject to exaggerated lateral or side-to-side vibration during use. In order to dampen or limit the lateral side-to-side vibration of the third region 30, an external dampering member, such as a sheath 40, may be applied to such region 30 to limit its propensity for lateral side-to-side movement. As shown in FIG. 6, the preferred sheath member 40 comprises a segment of plastic tubing surrounding the entire third region 30 of ultrasound transmission member 22. The inner diameter (ID) of sheath member 40 is sized relative to the ultrasound transmission member 22 such that the proximal and distal ends of the sheath member 40 are flush with and engage the adjacent outer surfaces of the second region 28 and fourth region 32 of the ultrasound transmission member 22, as shown. Adhesive 42 is utilized to bond, at least the end portions of sheath member 40 to the adjacent outer surfaces of the ultrasound transmission member 22.

The inner diameter of sheath 40 is larger than the outer diameter of third region 30 such that a space 44 exists therebetween. Space 45 may optionally be filled with matter capable of damping or inhibiting lateral side-to-side movement of the third region 30. Examples of damping material which may be disposed within space 45 include RTV silicone or other elastic materials such as natural or synthetic rubber. As an alternative, the quantity of adhesive 42 may be increased such that the adhesive 42 fills the entire space 45 between the outer surface of the third region 30 and the inner diameter of sheath 40. In such embodiments, it will be recognized that adhesion of the adhesive 42 to the outer surface of the third region 30 may limit the desirable longitudinal vibration of the third region 30, in addition to the undesirable lateral or side-to-side vibration thereof. To avoid such adhesion to the third region 30, anti-adhesive materials or release agents may be applied to the third region 30 prior to disposition of the adhesive 42, thereby preventing the adhesive 42 from adhering to the outer surfaces of the third region 30, while permitting the adhesive to form the desirable bond with the adjacent surfaces of the second region 28 and fourth region 32 so as to hold sheath 40 firmly in place.

As shown in FIGS. 3–4, the catheter body comprises a hollow tube having a longitudinal bore or lumen 44 extending therethrough. A rigid distal head or endcap 48 is inserted to the distal end of the catheter body 20. In the embodiment shown, the distal head 40 has a generally smooth rounded outer configuration so as to form a blunt tip which is flush and continuous with the adjacent outer surface of the catheter body 20. A blind cul de sac or bore 46 is formed in the proximal side of the distal head 48 to receive the distal end of the ultrasound transmission member 22 therein. As shown, the distal end of the ultrasound transmission member 22 is inserted part way into bore 46 and may be welded, adhered or mechanically engaged thereto so as to hold distal head 48 in its desired longitudinal position within the distal end of the catheter body 20 and also to form abutting contact between the distal end of the ultrasound transmission member 22 and the distal head 48. As such, ultrasonic vibration which passes distally through the ultrasound transmission member 22 will be transmitted into the distal head 48, thereby causing distal head 48 to vibrate in accordance with the energy transmitted through ultrasound transmission member 22.

Also in the embodiment of the catheter shown in FIGS. 3–4, a guide wire lumen 50 extends through the distal head 48 and partially through a distal portion of the catheter body. A guide wire (phantom lines) may be passed through the guide wire lumen to facilitate insertion and positioning of the catheter 10.

The guide wire lumen 50 is at least partially defined by the inner lumen of a tube 52. The guidewire lumen 50 extends through a longitudinal bore formed in the distal head 48 and through a distal portion of the lumen 44 of the catheter body 20. The proximal end of tube 52 is flush with and may be bonded to the sidewall of the catheter 20, thereby forming sidewall guide wire aperture 54 in catheter body 20.

Also, in the embodiment shown, dual infusion apertures 56 extend longitudinally through distal head 48 in fluidic communication with the hollow bore 44 of catheter 20. A fluid infusion sidearm 58 is formed in the proximal end connector assembly 24 to permit infusion of fluid through the bore of the proximal connector assembly 24 and through the hollow lumen 44 of the catheter 20 such that said fluid will pass out of the dual infusion apertures 55 located in the distal head 48 of the device. Such passage of fluid through the catheter 20 may be for purposes of cooling or controlling the temperature of the ultrasound transmission member 22 and/or may also be for purposes of providing an infusion of irrigation fluid, radiographic contrast media, oxygenated perfusate and/or medicaments.

Figure 7:
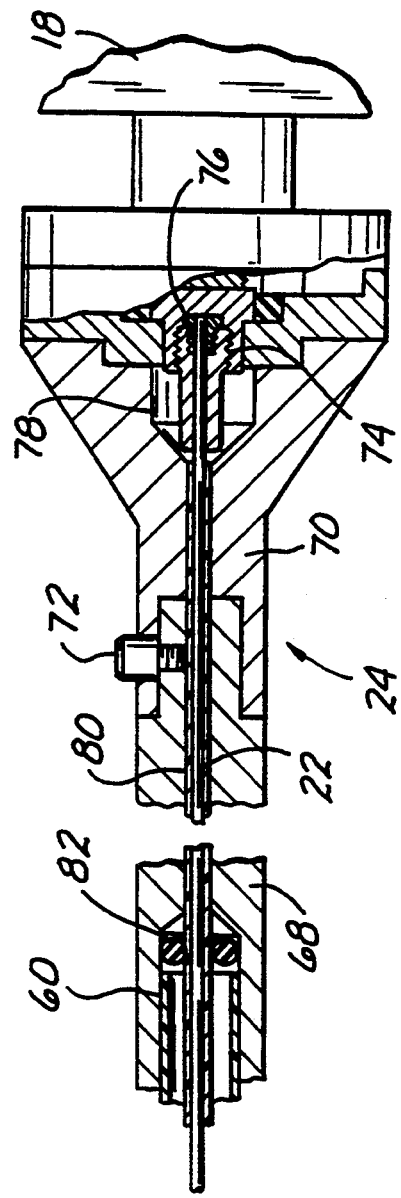
FIG. 7 is a longitudinal sectional view of a portion of the proximal end connector assembly of the catheter shown in FIG. 1.

One type of proximal connector assembly 24 which may be utilized as part of the catheter device 10 is shown, in detail, in FIGS. 1 and 7. The proximal connector 24 shown in FIGS. 1 and 7 comprises an elongate, rigid body defining a frontal portion, a mid-portion 60 and a rear portion 62. The frontal portion 59 of the elongate body is firmly connected to the proximal end of the catheter body 20 by way of a threaded gripping member 64 engaged thereto. In this respect, the proximal end of the catheter body 20 preferably has a flared configuration and includes an annular flange formed on the outermost end thereof which is brought into sealed engagement with the connector assembly 24 when the gripping member 64 is threadably engaged to the body 56. The proximal end of the frontal portion 59 is connected to the distal end of the mid-portion 60 of the elongate body by way of a second gripping member 66. As will be recognized, to facilitate the aforementioned construction, threads are formed on the distal ends of the frontal portion 58 and the mid-portion 60. Additionally, as seen in FIG. 7, the proximal end of the mid-portion 60 is non-threaded and is slidably received into a corresponding bore formed in the distal end of the rear portion 62 of the body 56. In this respect, the mid-portion 60 is maintained in engagements to the rear portion 62 via the utilization of an adhesive or other suitable affixation method.

Referring further to FIG. 7, the rear portion 62 of the body 56 comprises a distal member 68, the distal end of which is adapted to receive the proximal end of the mid-portion 60, and a generally frusto-conical proximal member 70. The proximal end of the distal member 68 is formed of a reduced diameter and is slidably inserted into a complimentary recess defined in the distal end of the proximal member 70. The proximal member 70 is maintained in engagement to the distal member 68 via the utilization of a threaded fastener 72 such as a screw which is extended through the bore defining wall of the proximal member 70 and into a threaded aperture disposed within the reduced diameter end of the distal member 68. The ultrasound transmission member 22 extend longitudinally through the entire catheter portion 11 and through the proximal end of the connector assembly 12. The ultrasound transmission member 22 are then inserted into and engaged by a threaded proximal connector 74 which is positioned within a cylindrical recess formed in the proximal end of the proximal member 70. The ultrasound transducer 18 is cooperatively engaged to the proximal connector 74 in a manner adapted to accomplish the passage of ultrasonic energy through the ultrasound transmission member 22 in a distal direction to the distal end of the catheter body 20.

The extreme proximal end of the proximal member 70 is provided with a sonic connector assembly or apparatus configured to effect operative attachment of the proximal ends of the ultrasound transmission member 22 to the horn of the ultrasound transducer 18. The sonic connector assembly or apparatus is preferably configured and constructed to permit passage of ultrasound energy through the ultrasound transmission member 22 with minimal lateral side-to-side movement of the ultrasound transmission members 22 while, at the same time, permitting unrestricted longitudinal forward/backward vibration or movement of the ultrasound transmission member 22. Specifically, a distal portion of the body of the threaded proximal connector 74 is configured to receive therein a compressible gripping ferrule 76. The compressible gripping ferrule 76 has a small central aperture formed therethrough through which the ultrasound transmission member 22 passes, as shown. A frontal member 78 is threadably tightened within the frontal portion of the body of the proximal connector 74 so as to compress the gripping ferrule 76, thereby causing the gripping ferrule 76 to firmly grip and hold the ultrasound transmission member 22 in place within the body of the proximal connector 74. The proximal connector 74 may then be compressed or crimped inwardly so as to be additionally crimp connected or crimp fit to the proximal ends of the ultrasound transmission member 22, thereby providing further gripping and attachment of the sonic connector assembly to the proximal ends of the ultrasound transmission member 22. The proximal connector 74 is further formed to permit the distal end of the ultrasound transducer horn to be releasably engaged thereto and thus releasably attached to the sonic connector assembly. Thus, the frontal member 78, gripping ferrule 76, and proximal connector 74 combine to form a sonic connector assembly to which the horn of the ultrasound transducer 18 may be attached and through which the ultrasonic energy may be transmitted into the ultrasound transmission member 22. A lumen 80 extending through the rear and mid-portions 62, 60 of the connector assembly 24 is specifically sized to be large enough to permit the ultrasound transmission member 22 to pass therethrough with a small amount of space remaining between the outer surfaces of the ultrasound transmission member 24 and the innerlumenal surface of the lumen. Also disposed within the mid-portion receiving bore formed in the distal end of the distal member 68 is on O-ring 82 which is used to prevent the passage of any fluid along the outer surfaces of the lumen 80 into the proximal member 70 of the rear portion 62.

B. Operation of the Preferred Embodiment

In operation, the catheter 20 described here above may be inserted percutaneously, or otherwise, into a desired anatomical structure such as a blood vessel. The proximal connector assembly 24 of the device will then be connected to ultrasound transducer 18. Depression of on/off foot pedal 59 will cause signal generator 14 to emit a desired electrical signal through cable 16 to ultrasound transducer 18. Ultrasound transducer 18 will convert the received electrical signal to ultrasonic vibration and such ultrasonic vibration will be passed through ultrasound transmission member 22 to the distal head 48 of the catheter 10.

As the ultrasonic energy passes from the first region 26 of the ultrasound transmission member 22 into the second region 28 thereof, the narrowing or taper of the second region 28 will result in an increase in the amplitude of the ultrasonic energy passing therethrough. Thereafter, as the ultrasonic energy passes through the constant diameter third region 30 of the ultrasound transmission member 22 the amplitude will remain substantially constant. Thereafter, as the ultrasound energy passes from the third region 30 to the outwardly tapered or enlarging fourth region 32, the amplitude of the ultrasound will again decrease in accordance with the change in outer diameter of the ultrasound transmission member 22.

Although the invention has been described herein with specific reference to presently preferred embodiments thereof, it will be appreciated by those skilled in the art that various additions, modifications, deletions and alterations may be made to such preferred embodiments without departing from the spirit and scope of the invention. For example, the ultrasound transmission member of the present invention may be positioned within many different catheters which differ in configuration and construction from the preferred catheter shown in this patent application or, the ultrasound transmission member of the present invention may be positioned in, or incorporated in, a guide wire or may be utilized independent of any surrounding catheter sheath as described herein with respect to the preferred embodiment. Accordingly, it is intended that all reasonably foreseeable additions, deletions, alterations and modifications be included within the scope of the invention as defined in the following claims.

What is claimed is:

1. An ultrasound transmission member coupleable to an ultrasound generating device for transmitting ultrasound from said ultrasound generating device to a location within a mammalian body, said ultrasound transmitting member comprising:
   an elongate member having a proximal end, distal end, and at least four regions of differing cross-sectional dimension, said four regions of said elongate member comprising:
   i) a first region extending distally from the proximal end of the member and having a substantially continuous first cross-sectional dimension;
   ii) a second region extending distally from the distal end of said first region, said second region being tapered to a second cross-sectional dimension smaller than said first cross-sectional dimension;
   iii) a third region extending distally from the distal end of said second region, said third region being of a substantially continuous third cross-sectional dimension, said third cross-sectional dimension being substantially the same as said second cross-sectional dimension; and
   iv) a fourth region extending distally from, the distal end of said third region, said fourth region being tapered to a fourth cross-sectional dimension larger than said third cross-sectional dimension.

2. The ultrasound transmission member of claim 1 wherein said second region further comprises:
   a first proximal portion tapered from said first cross-sectional dimension to an intermediate cross-sectional sectional dimension between said first cross-sectional dimension and said second cross-sectional dimension;
   an intermediate portion of substantially consistent cross-sectional dimension equal to said intermediate cross-sectional dimension; and
   a distal portion further tapered from said intermediate cross-sectional dimension to said second cross-sectional dimension.

3. The ultrasound transmission member of claim 1 wherein said second region comprises a continuous gradual taper from said first cross-sectional dimension to said second cross-sectional dimension.

4. The ultrasound transmission member of claim 1 wherein said fourth region further comprises:
   a first proximal portion tapered from said third cross-sectional dimension to said fourth cross-sectional dimension; and
   a distal portion of substantially continuous cross-sectional dimension equal to said fourth cross-sectional dimension.

5. The ultrasound transmission member of claim 1 wherein said first region is approximately 53.0 inches in length.

6. The ultrasound transmission member of claim 1 wherein said first cross-sectional dimension is approximately 0.030 inches diameter.

7. The ultrasound transmission member of claim 1 wherein said second region is approximately 8.95 inches in length.

8. The ultrasound transmission member of claim 1 wherein said second cross-sectional dimension is approximately 0.14 inches diameter.

9. The ultrasound transmission member of claim 1 wherein said third region is approximately 0.750 inches in length.

10. The ultrasound transmission member of claim 1 wherein said third cross-sectional dimension is approximately 0.10 inches diameter.

11. The ultrasound transmission member of claim 1 wherein said fourth region is approximately 0.300 inches in length.

12. The ultrasound transmission member of claim 1 wherein said fourth cross-sectional dimension is approximately 0.014 inches diameter.

13. The ultrasound transmission member of claim 2 wherein said first cross-sectional dimension of said first region is 0.030 and wherein:
   said first proximal portion of said second region is tapered downwardly from said first cross-sectional dimension of 0.030 inches to an intermediate cross-sectional dimension of 0.014 inches;
   said intermediate portion of said second region is of substantially continuous cross-sectional dimension of 0.014 inches; and
   said distal portion of said second region is further downwardly tapered from said intermediate cross-sectional dimension of 0.014 inches to said second cross-sectional dimension of 0.010 inches.

14. The ultrasound transmission member of claim 2 wherein:

said first proximal portion of said second region is approximately 2.5 inches in length;

said intermediate portion of said second region is approximately 6.20 inches in length; and said distal portion of said second region is approximately 0.250 inches in length.

15. The ultrasound transmission member of claim 4 wherein said third cross-sectional dimension of said third region is approximately 0.10 inches and wherein:

said first proximal portion of said fourth region is gradually tapered from said third cross-sectional dimension of approximately 0.10 inches to a fourth cross-sectional dimension of approximately 0.014 inches; and said distal portion of said fourth region is continuously of said fourth cross-sectional dimension of approximately 0.014 inches.

16. The ultrasound transmission member of claim 4 wherein:

said first proximal portion of said fourth region is approximately 0.250 inches in length; and said second distal portion of said fourth region is approximately 0.50 inches in length.

17. The ultrasound transmission member of claim 1 wherein said ultrasound transmission member is formed of a superelastic metal alloy.

18. The ultrasound transmission member of claim 17 wherein said super elastic metal alloy comprises nickel titanium alloy having 50.8 atomic percent nickel.

19. An ultrasound transmission member coupleable to an ultrasound generating device for transmitting ultrasound from said ultrasound generating device to a location within a mammalian body, said ultrasound transmitting member comprising:

an elongate member having a proximal end, a distal end, and at least four regions of differing cross-sectional dimensions, said four regions of said elongate member comprising:

i) a first region extending distally from the proximal end of the member and having a substantially continuous first cross-sectional dimension;

ii) a second region extending distally from the distal end of said first region, said second region being tapered to a second cross-sectional dimension smaller than said first cross-sectional dimension;

iii) a third region extending distally from the distal end of said second region, said third region being of a substantially continuous third cross-sectional dimension said third cross-sectional dimension being substantially the same as said second cross-sectional dimension;

iv) a fourth region extending distally from, the distal end of said third region, said fourth region being tapered to a fourth cross-sectional dimension larger than said third cross-sectional dimension; and v) a dampening member disposed about said third region to dampen transverse side-to-side vibrational movement in said third region, said dampening member comprising a sheath.

20. The ultrasound transmission member of claim 19 where said dampening member comprises a tube surrounding said third region.

21. The ultra sound transmission member of claim 20 further comprising an adhesive for affixing said tube to said ultrasound transmission member.

22. The ultrasound transmission member of claim 20 wherein said tube is slightly longer than said third region, said tube having a proximal end in abutting contact with the adjacent second region and a distal end in abutting contact with the adjacent the fourth region.

23. The ultrasound transmission member of claim 20 wherein said tube has a hollow inner bore which is larger than said third cross-sectional dimension of said third region such that space exists between said third region and said tube.

24. The ultrasound transmission member of claim 23 wherein a quantity of damping material is disposed within said space between said third region and said tube.

25. The ultrasound transmission member of claim 24 wherein said damping material comprises a resilient polymer.

26. The ultrasound transmission member of claim 24 wherein said damping material comprises a liquid.

27. The ultrasound transmission member of claim 24 wherein said damping material is selected from the group consisting of:

a) RTV silicone;

b) natural rubber; and c) synthetic rubber;

28. An ultrasound catheter comprising:

an elongate flexible catheter sheath having a distal end, a proximal end, and a hollow lumen extending longitudinally therethrough; and an ultrasound transmission member extending longitudinally through the lumen of said catheter sheath, said ultrasound transmission member comprising:

an elongate member having a proximal end, a distal end, and at least four regions of differing cross-sectional dimension, said four regions of said elongate member comprising:

i) a first region extending distally from the proximal end of the member and having a substantially continuous first cross-sectional dimension;

ii) a second region extending distally from the distal end of said first region, said second region being tapered to a second cross-sectional dimension smaller than said first cross-sectional dimension;

iii) a third region extending, distally from the distal end of said second region, said third region being of a substantially continuous third cross-sectional dimension, said third cross-sectional dimension being substantially the same as said second cross-sectional dimension; and iv) a fourth region extending distally from, the distal end of said third region, said fourth region being tapered to a fourth cross-sectional dimension larger than said third cross-sectional dimension.

29. The ultrasound catheter of claim 28 further comprising:

a distal head member connected to the distal end of said ultrasound transmission member and configured so as in abutting contact with the distal end of said catheter sheath.

* * * * *